United States Patent [19]

Holloway

[11] 4,342,830
[45] Aug. 3, 1982

[54] PROCESS FOR SEPARATING AND RECOVERING ORGANICS AND INORGANICS FROM WASTE MATERIAL

[75] Inventor: Clifford C. Holloway, 303 E. Brooks, Apt. 215 W, Norman, Okla. 73069

[73] Assignees: Clifford C. Holloway; Lewis B. Holloway; Winford B. Holloway, all of Birmingham, Ala. ; a part interest

[21] Appl. No.: 262,316

[22] Filed: May 11, 1981

[51] Int. Cl.³ .......................... C12P 7/06; C12P 7/08; A23K 1/10
[52] U.S. Cl. .................................. 435/161; 435/163; 435/165; 426/635; 426/807; 71/14
[58] Field of Search ................ 426/479, 14, 635, 807; 435/161, 163, 165; 71/14, 22, 23

[56] References Cited

U.S. PATENT DOCUMENTS

| | | | |
|---|---|---|---|
| 1,307,991 | 6/1919 | Wells | 435/163 |
| 1,440,727 | 1/1923 | Faust | 435/165 |
| 3,653,871 | 4/1972 | Tempe | 71/14 X |
| 4,093,516 | 6/1978 | Lang | 435/161 X |
| 4,094,740 | 6/1978 | Lang | 435/163 X |
| 4,288,550 | 9/1981 | Ishida et al. | 435/163 X |

*Primary Examiner*—Robert A. Yoncoskie
*Attorney, Agent, or Firm*—Woodford R. Thompson, Jr.

[57] ABSTRACT

A process for recovering organics and inorganics from waste material with a specific object of preparing the separated organic fraction for the production of ethanol wherein rigid organic matter becomes soft when subjected to heat and pressure. The process is carried out by first, feeding the waste material into a perforated container mounted within a closed chamber. Next, the waste material is agitated and subjected to heat and pressure which sterilizes it and softens the organics contained therein. After heating under pressure, the pressure is suddenly released from the chamber which forces the softened organics outwardly of the container, thus separating them from the inorganics for further processing to recover fuels and animal feed supplements.

10 Claims, 1 Drawing Figure

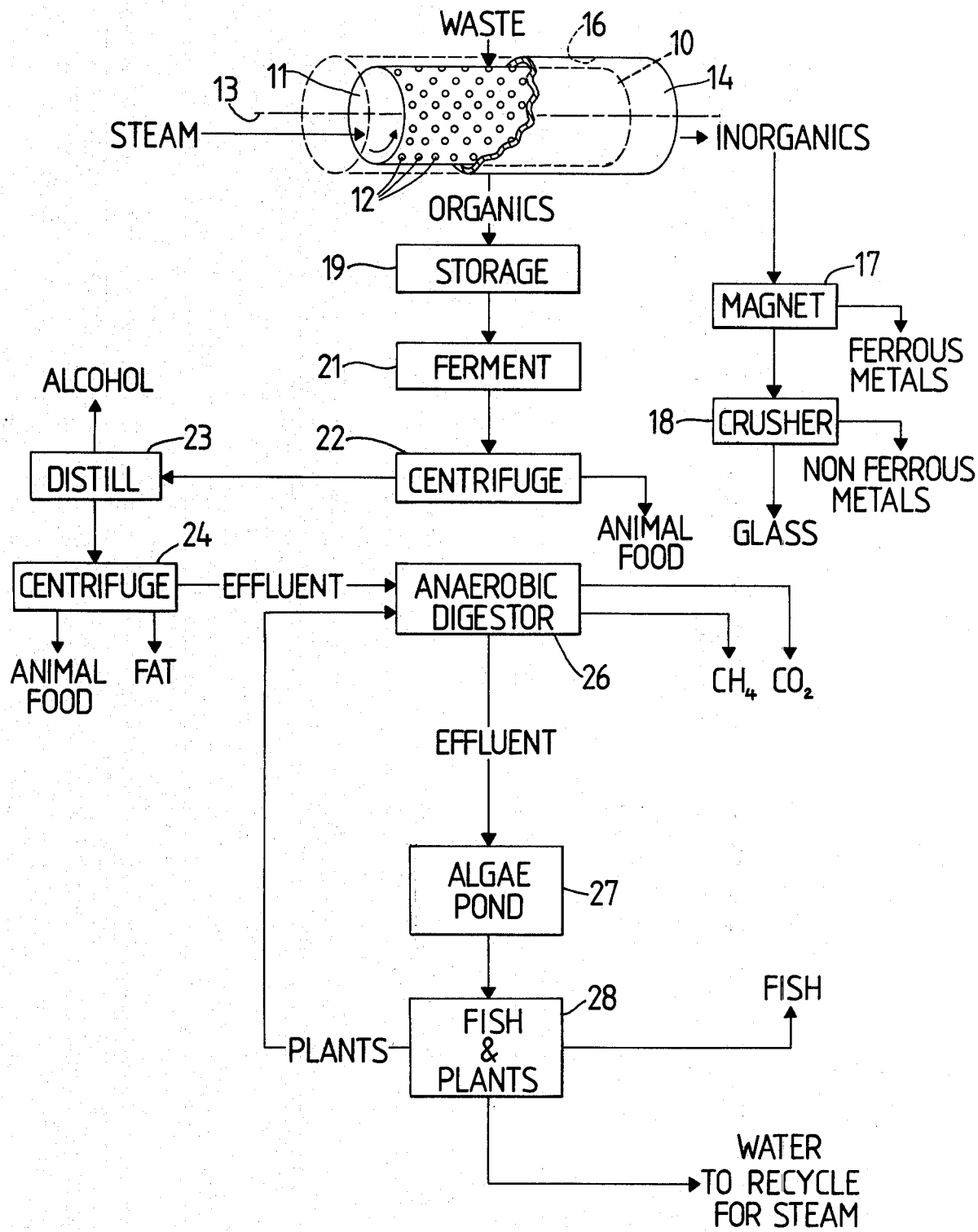

PROCESS FOR SEPARATING AND RECOVERING ORGANICS AND INORGANICS FROM WASTE MATERIAL

BACKGROUND OF THE INVENTION

This invention relates to a process for treating waste material and more particularly to a process for treating waste material such as commercial, industrial, agricultural, household and restaurant waste for the recovery of useful organic and inorganic matter contained therein, and with a specific object of preparing the separated organic matter for the production of ethanol.

Heretofore, various methods have been devised for the treatment and disposal of waste material including landfill, ocean dumping, composting, heat treatment and incineration. Also, waste food scraps from commercial catering establishments have in the past been fed to animals as a method of disposal, but in recent years this has been discouraged due to the fear of introducing disease to such animals. With the tremendous increase in the volume of waste produced, such methods have become environmentally unsafe, inefficient and very expensive.

Furthermore, conventional recycling processes used in cooperation with such disposal methods only separate out the solids from the remainder of the waste and reduce the size thereof for the recovery of ferrous metals and other useful solids such as glass and the like contained therein. This may be accomplished by subjecting the solids to magnets for the recovery of ferrous metals or by subjecting them to crushers and hammer mills for size reduction. Also, the solids may be passed through fluids moving at various speeds whereby they are separated and classified according to density and aerodynamic qualities. Such conventional recovery processes have only achieved limited success due to the fact that they recover only limited amounts of reusable material with waste material still remaining for disposal.

SUMMARY OF THE INVENTION

In accordance with my invention, I provide a process for treating waste material for the recovery of organic and inorganic matter which is safer and more reliable than the methods mentioned above. My improved process is simple and economical of operation and recovers more useful material than any conventional method with which I am familiar.

It is an object of my invention to provide an efficient waste recovery process that is adapted to treat various types of waste material such as paper, plastic, metal, glass, waste food, wood chips and the like for the recovery of useful organic and inorganic matter.

My improved process will significantly reduce the overload of waste material going to landfills and sewage plants by recovering not only solid inorganic matter but organic matter as well.

The improved process is carried out by feeding the waste material into a perforated container mounted within a closed chamber. The container is then agitated by suitable means, such as by rotation, as the chamber is subjected to pressure and heat to sterilize the waste material and soften the organic matter contained therein. The chamber is then depressurized whereupon the softened organic matter is forced out of the container through its perforations, leaving only inorganic matter therein. The organic matter is further treated for the recovery of animal feed supplements and liquid and gaseous fuels. The inorganic matter is separated into glass, ferrous and non-ferrous materials.

DESCRIPTION OF THE DRAWING

Apparatus embodying features of my invention and which may be employed to carry out my improved process is shown in the accompanying drawing, forming a part of this application, in which:

The single view is a schematic diagram of my improved system.

DETAILED DESCRIPTION

Referring now to the drawing for a better understanding of my invention, I show waste material, such as industrial, commercial, agricultural or household garbage being fed into a perforated drum or container 10 having closed ends 11 and perforations 12 at the sides thereof. In actual practice I have found that a container 10 cylindrical in shape and having ¾ inch perforations at its sides is satisfactory. The container 10 is shown as being mounted for rotation about its longitudinal axis 13 inwardly of a closed chamber 14 and in spaced relation to the inner surface 16 thereof as shown.

After the waste material is fed into the container 10, it is subjected to heat and pressure by suitable means, such as by introducing steam into the closed chamber 14 for a period ranging from approximately twenty minutes to two hours to bring the pressure therein up to a pressure ranging from approximately 20 psi to 100 psi. The waste material is thus biologically sterilized and the organic matter, such as vegetable matter, bones, meat scraps, paper and the like, are softened and partially hydrolized. In actual practice, I have found that when the steam is introduced into the chamber 14 at a pressure of approximately 60 psi for approximately one hour, the process operates satisfactorily in every respect with household garbage and food scraps from restaurants. During the steam injection period, the container 10 is agitated, such as by rotating it about its longitudinal axis 13 within the chamber 14 by a conventional drive unit, not shown.

After the waste material is sterilized and the organic matter softened, the pressure within the chamber 14 is released suddenly whereby the organic matter is separated from the inorganic matter such as bottles, cans, ceramics and the like. This is accomplished due to the sudden depressurization within the chamber 14 which causes the softened organic matter to be forced out of the container 10 through the perforations 12 with only solid inorganic matter being left therein.

The solid inorganic matter is removed from the container 10 by suitable means for further processing and separation into useful glass, ferrous and non-ferrous materials. This is accomplished by passing the solids over a magnet 17 to remove the ferrous metals and then introducing the remainder thereof to a conventional crusher 18 where the glass is shattered and recovered from non-ferrous metals for reuse in a manner well understood in the art.

The softened organic matter is shredded and broken up as it is forced through the perforations 12 and is then transferred to a conventional storage container 19 where suitable additives, such as acids, alkali or enzymes may be added. The shredded and treated organic matter is transferred from the storage container 19 to a fermentation chamber 21 where it is fermented with yeast or bacteria in a conventional manner to form an ethanol-containing mash.

The mash is separated into liquid and solid portions by passing it through a conventionl centrifuge 22. This solid portion contains high nutritional value and is preferably recovered for use as an animal feed supplement. This may be accomplished by feeding in a wet state to form a wet feed or by drying the solid portion in a conventional manner to a moisture content not greater than approximately 13% by weight. After drying, the solid portion is passed through a conventional milling apparatus such as a hammer mill where it is pulverized into a meal or granular type substance with high protein content.

The separated liquid portion of the mash is passed to a distillation column 23 for the recovery of ethanol, with the residue therefrom being transferred to a second centrifuge 24 for the recovery of fats and animal feed before passing the solubles into an anaerobic digester 26. To aid in the production of ethanol, acid, such as hydrochloric acid, alkali or enzymes, may be added to the organic matter prior to fermentation. This will enhance the hydrolysis of the polysaccharide materials contained therein. In the anaerobic digester 26, a "biogas" is produced and separated into carbon dioxide and methane in a conventional scrubber, not shown. In view of the fact that recovering methane, carbon dioxide and ethanol from the processes mentioned above is well known in the art, no further description is deemed necessary.

The effluent from the anaerobic digester 26 is transferred to an algae pond 27 where algae is grown from the remaining nutrients through photosynthesis. The contents of the algae pond 27 may be passed into a fish pond 28 where a portion of the algae is used primarily as a food for fish with the remainder being used for plant food. The plants may be harvested and returned to the anaerobic digester 26 while at the same time the water is being cleaned and recycled for use in steam production.

From the foregoing the operation of my improved process for treating waste material for the recovery of useful organic and inorganic matter will be readily understood. First, waste material is fed into the container 10. Next, steam is introduced into the closed chamber 14 to raise the pressure therein while the container 10 is agitated, such as by rotation. The waste material is treated until it is sterilized and the organic matter contained therein is softened. The pressure is then suddenly released whereby the softened organic matter is forced outwardly through the perforations 12 in the container 10, thus separating it from the solid inorganic matter contained therein. The solid inorganic matter is then removed from the container 10 and further processed and separated into useful glass, ferrous and non-ferrous materials as described above. The softened organic matter is removed from the chamber 14 and passed through a storage container 19 and then to a fermentation chamber 21 where it is fermented by yeast or bacteria to form an ethanol-containing mash. The mash is passed through a centrifuge 22 where it is separated into liquid and solid portions. The solid portion of the mash is dried and pulverized to form a meal-like product for use as an animal food supplement or may be used as a wet feed. The liquid portion is then passed to the distillation column 23 where ethanol is recovered. The residue from the distillation column is passed through a second centrifuge 24 where fats are recovered and the remainder is then passed to an anaerobic digester 26 for the recovery of methane and carbon dioxide. The fats may be recovered prior to fermentation or distillation.

The effluent from the digester 26 may then be passed on to an algae pond 27 where it aids in the growth of algae. A portion of the contents of the algae pond is then passed to the fish pond 28 whereby the algae is used as feed for fish with plants feeding on the remaining nutrients. The plants then may be harvested and returned to the anaerobic digester 26 to aid in the production of methane and carbon dioxide.

From the foregoing, it will be seen that I have devised an improved process for treating waste material which is simple and very economical to carry out. Also, my improved process permits waste material to be diverted from landfills and overloaded sewage systems and converted into useful and valuable fuels and supplements for animal feed.

While I have shown my invention in but one form, it will be obvious to those skilled in the art that it is not so limited, but is susceptible of various changes and modifications without departing from the spirit thereof.

What I claim is:

1. The process of treating waste material for the separation and recovery of organic matter comprising fermentable vegetable material and inorganic matter wherein rigid organic matter becomes soft when subjected to heat and pressure, comprising carrying out the following steps in the sequence named:
   (a) feeding said waste material into a container having perforations therein and mounted within a closed chamber in spaced relation to the inner surface of said closed chamber,
   (b) agitating said waste material while in said container,
   (c) subjecting said waste material in said container to heat under a pressure ranging from approximately 20 psi to 100 psi for a period ranging from approximately twenty minutes to two hours to sterilize said waste material and soften said organic matter contained therein, and
   (d) releasing the pressure from said chamber suddenly to thus force the softened organic matter outwardly of said container through said perforations, so that said organic matter is separated from said inorganic matter in said container.

2. The process for treating waste material as defined in claim 1 in which steam under pressure is introduced to heat and pressurize said waste material in said container.

3. The process as defined in claim 1 in which steam is introduced for a period of approximately one hour and at a pressure of approximately 60 psi.

4. The process for treating waste material as defined in claim 1 in which said inorganic matter is separated into ferrous and non-ferrous materials by subjecting it to a magnetic field to remove said ferrous material therefrom.

5. The process for treating waste material as defined in claim 1 in which said organic matter is fermented to form a mash.

6. The process for treating waste material as defined in claim 5 in which said organic matter is subjected to fermentation by yeast to form said mash.

7. The process for treating waste material as defined in claim 5 in which said organic material is subjected to fermentation by bacteria to form said mash.

8. The process for treating waste material as defined in claim 5 in which said mash is separated into a liquid portion and a solid portion, with said liquid portion being treated for the recovery of fuels and with said solid portion being treated for the recovery of animal feed supplements.

9. The process for treating waste material as defined in claim 8 in which said liquid portion is distilled for the recovery of ethanol with the residue thereof being fed into an anerobic digester for the recovery of methane.

10. The process for treating waste material as defined in claim 8 in which said solid portion is dried to a maximum moisture content of approximately 13% by weight.

* * * * *